United States Patent [19]

Le Polles et al.

[11] 4,442,108

[45] Apr. 10, 1984

[54] HYDROGENATED ISOQUINOLINES AND PERIPHERAL VASCULAR DISEASE TREATING COMPOSITIONS THEREOF

[75] Inventors: Jean-Bernard Le Polles, Rennes; Michel Martin, Saint-Gregoire; Guy Nadler, Rennes; Edmond Saias, Issy-les-Moulineaux, all of France

[73] Assignee: Laboratoires Sobio S.A. of Immeuble Perisud, France

[21] Appl. No.: 300,957

[22] Filed: Sep. 10, 1981

Related U.S. Application Data

[63] Continuation of Ser. No. 196,322, Oct. 14, 1980, abandoned, which is a continuation of Ser. No. 898,145, Apr. 20, 1978, abandoned.

[51] Int. Cl.$^3$ .................. C07D 215/14; A61K 31/47
[52] U.S. Cl. ................................ 424/258; 546/149
[58] Field of Search ................... 546/149; 424/258

[56] References Cited

U.S. PATENT DOCUMENTS 2,928,769 12/1955 Shepard .............................. 546/149
3,978,063 8/1976 Kishimoto et al. ................. 548/251

FOREIGN PATENT DOCUMENTS 1417542 10/1975 United Kingdom ............... 548/149

*Primary Examiner*—Paul M. Coughlan, Jr.
*Assistant Examiner*—D. B. Springer
*Attorney, Agent, or Firm*—Jacobs & Jacobs

[57] ABSTRACT

1-(3,4-Dialkoxybenzyl)-6,7-dialkoxyl-1,2,3,4-tetrahydro- and 3,4-dihydroisoquinolines wherein the alkoxy groups in the benzyl ring are different from those in the isoquinoline nucleus and one contains from 2 to 6 carbon atoms while the other contains from 3 to 6 carbon atoms are useful in the treatment of peripheral vascular disease. A typical embodiment is 1-(3,4-diethexybenzyl)-6,7-diisopropoxy-3,4-dihydroisoquinoline hydrochloride.

7 Claims, No Drawings

HYDROGENATED ISOQUINOLINES AND PERIPHERAL VASCULAR DISEASE TREATING COMPOSITIONS THEREOF

CROSS-REFERENCE

This is a continuation of Ser. No. 196,322 filed Oct. 14, 1980, abandoned which is a continuation of Ser. No. 898,145 filed Apr. 20, 1978, abandoned.

DETAILED DESCRIPTION

This invention relates to a class of hydrogenated benzylisoquinoline derivatives which possess spasmolytic and hypotensive activity.

British Pat. No. 1,417,542 discloses the use of certain hydrogenated isoquinoline derivatives of formula (I):

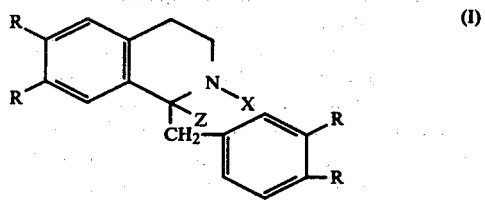

(wherein each R independently represents hydrogen or an alkoxy group containing 1–10 carbon atoms; and Z and X each represent hydrogen or together form a valency bond) in the form of their theophylline 7-acetate salts, for geriatric use. The compounds disclosed in British Pat. No. 1,417,542 have each group R being identical to each other, a preference being stated for the tetra-ethoxy compound.

We have now found that hydrogenated benzylisoquinoline derivatives having higher alkoxy substituents on the aromatic rings, and having such substituents on one ring different to those on the other ring, have superior properties to known compounds.

Accordingly the present invention provides a compound of formula (II), or a pharmaceutically acceptable acid addition salt thereof:

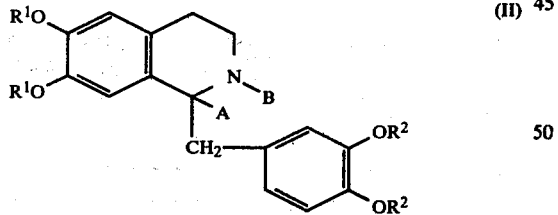

wherein $R^1$ and $R^2$ are different and one represents a $C_1$–$C_6$ alkyl group and the other represents a $C_3$–$C_6$ alkyl group; and A and B either both represent hydrogen or together represent a covalent bond.

The groups $R^1$ and $R^2$ may be, for example ethyl, n- or iso-propyl, or n-, iso-, sec- or tert-butyl. Preferably, one of $R^1$ and $R^2$ represents isopropyl.

Pharmaceutically acceptable acid addition salts of compounds of formula (II) are also included within this invention. Suitable acid addition salts of the compounds of formula (II) include, for example inorganic salts such as the sulphate, nitrate, phosphate, and borate; hydrohalides e.g. hydrochloride, hydrobromide and hydroiodide; and organic acid addition salts such as acetate, oxalate, tartrate, maleate, citrate, succinate, benzoate, ascorbate, methanesulphonate and p-toluenesulphonate.

Specific compounds within the scope of the present invention include the following:

6,7-diethoxy-1-(3',4'-diisopropoxybenzyl)-3,4-dihydroisoquinoline, or its hydrochloride;

1-(3',4'-diethoxybenzyl)-6,7-diisopropoxy-3,4-dihydroisoquinoline, or its hydrochloride or ascorbate;

6,7-diethoxy-1-(3',4'-di-n-propoxybenzyl)-3,4-dihydroisoquinoline, or its hydrochloride;

1-(3',4'-diethoxybenzyl)-6,7-di-n-propoxy-3,4-dihydroisoquinoline, or its hydrochloride;

1-(3',4'-diethoxybenzyl)-6,7-diisopropoxy-1,2,3,4-tetrahydroisoquinoline or its hydrochloride;

6,7-diethoxy-1-(3',4'-diisopropoxybenzyl)-1,2,3,4-tetrahydroisoquinoline or its hydrochloride.

A preferred compound of this invention is the hydrochloride of 1-(3',4'-diethoxybenzyl)-6,7-diisopropoxy-3,4-dihydroisoquinoline of formula (III):

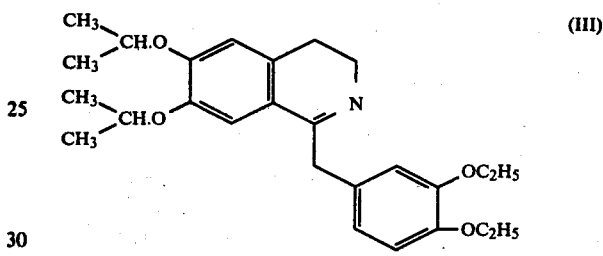

The compounds of the present invention may be prepared by a process which comprises (a) cyclisation of a compound of formula (IV):

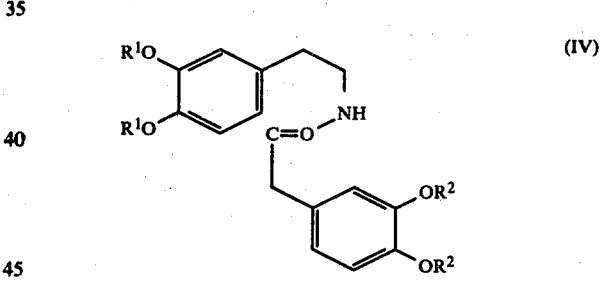

with a condensing agent (to produce a compound of formula (II) in which A and B together represent a bond); and (b) optionally reducing the resultant product (to produce a compound of formula (II) in which A and B are both hydrogen).

For step (a) of the above process, suitable condensing agents include phosphorus oxychloride and phosphorus pentoxide, preferably the former. The reaction is suitably carried out in a non-polar organic solvent such as benzene or chloroform, preferably under an inert atmosphere, e.g. nitrogen, at an elevated temperature e.g. 50°–100° C.

The reduction step, step (b) of the above process may be carried out using catalytic hydrogenation in the presence of palladium, Raney-nickel or a precious metal as catalyst. Suitably, palladium on charcoal is employed and the reduction carried out at a pressure of 1–10 atmospheres in the presence of a polar solvent. Hydrogenation may also be carried out by employing sodium amalgam or sodium in alcohol. A preferred method of carrying out the reduction of step (b) above is to employ a metallic hydride, especially lithium aluminium hydride in an organic solvent such as ether or tetrahydrofuran or sodium borohydride, in solution in a polar solvent e.g. an alkanol such as methanol or ethanol.

The amides of formula (IV) are novel compounds and form a further aspect of this invention. They may be prepared by known methods for preparing amides, for example by reacting a phenylethylamine of formula (V) with a compound of formula (VI):

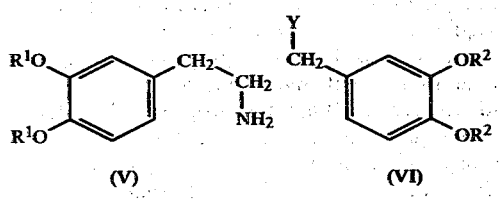

wherein Y represents a carboxylic acid group or an ester thereof, preferably an ethyl ester. This reaction is conveniently carried out without solvent at a temperature of from 120°–210° C.

The compounds according to the invention may be formulated for administration in any convenient way, and the invention therefore includes within its scope a pharmaceutical composition comprising a compound of formula (II) above together with a pharmaceutical carrier or excipient.

The compositions may be formulated for administration by any route, such as oral topical or parenteral. The compositions may be in the form of tablets, capsules, powders, granules, lozenges, creams of liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or accetable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired convent on flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg. of the active ingredient. The dosage as employed for adult human treatment will preferably range from 20–500 mg. per day, for instance 100 mg. per day, depending on the route and frequency of administration.

The following Examples illustrate the preparation of a number of compounds of this invention.

EXAMPLE 1

(a) N-[2-(3,4-diethoxyphenyl)ethyl]-3,4-diisopropoxyphenyl acetamide

A mixture of 2-(3,4-diethoxyphenyl)-ethylamine (40.7 g, 0.195 mole) and ethyl 3,4-diisopropoxyphenylacetate (55.7 g, 0.195 mole) was heated with stirring at 160° C. for 20 hours, allowed to cool and the resulting oil taken up in 700 ml of chloroform. The organic solution was washed 3 times with 100 ml of N hydrochloric acid and then with water to pH 7. The chloroform solution was dried over magnesium sulphate, the solvent removed under reduced pressure and purification effected by chromatography over silica gel. 64.5 g (yield 72%) of product was obtained sufficiently pure to be used in step (b) below.

By re-crystallisation of a sample in cyclohexane N-[2(3,4-diethoxyphenyl)ethyl]-3,4-diisopropoxyphenyl-acetamide is obtained, m.p.=87° C.

Analysis $C_{26}H_{37}NO_5 = 443.6$

|  | C % | H % | N % |
|---|---|---|---|
| Calculated | 70.40 | 8.41 | 3.16 |
| Found | 70.49 | 8.22 | 3.13 |

(b) 6,7-Diethoxy-1-(3'4'-diisopropoxybenzyl-3,4-dihydroisoquinoline hydrochloride 5.0 g (0.0113 mole) of N-[2-(3,4-diethoxyphenyl)ethyl] 3,4-diisopropoxyphenyl acetamide, 100 ml of benzene and 2.3 g (0.015 mole) of phosphorus oxychloride were introduced successively into a 250 ml flask. The reaction mixture was placed under a nitrogen atmosphere and heated under reflux for 2 hours. 70 ml of solvent was removed under reduced pressure, 30 ml of ethanol was added, followed by 1 ml of 12 N hydrochloric acid. A further 10 ml of solvent was removed, 20 ml of sodium-dried diethyl ether was added and the flask cooled externally to below −20° C. over a period of several hours. The crystallised product was drained under vacuum and washed 3 times with ether. Yield = 80%, m.p. 216° C.

Analysis $C_{26}H_{35}NO_4HCl = 462.0$

|  | C % | H % | N % | Cl % |
|---|---|---|---|---|
| Calculated | 67.59 | 7.85 | 3.03 | 7.67 |
| Found | 67.50 | 7.83 | 3.13 | 7.76 |

EXAMPLE 2

(a) N-[2-(3,4-Diisopropoxyphenyl)ethyl]-3,4-diethoxyphenylacetamide was prepared starting from 2-(3,4-diisopropoxyphenyl)ethylamine and ethyl 3,4-diethoxyphenyl acetate using the process described in Example 1 (a). Yield=67%, m.p. 71° C.

Analysis $C_{26}H_{37}NO_5 = 443.6$.

|  | C % | H % | N % |
|---|---|---|---|
| Calculated | 70.40 | 8.41 | 3.16 |
| Found | 70.73 | 8.09 | 3.07 |

(b) 1-(3'4'-Diethoxybenzyl)-6,7-diisopropoxy-3,4-dihydroisoquinoline hydrochloride 5.0 g (0.0113 mole) of N-[2-(3,4-diisopropoxyphenyl)-ethyl]-3,4-diethoxyphenylacetamide, 100 ml benzene, and 2.3 g (0.015 mole) of phosphorus oxychloride were introduced successively into a 250 ml 3-necked flask after being passed through an atmosphere of nitrogen. The mixture was heated under reflux with stirring over a period of 2 hours, 70 ml of solvent removed by distillation, 30 ml of ethanol, 1 ml of 12 N hydrochloric acid added and the bulk of solvent removed by distillation under reduced pressure. The residue obtained was washed several times with ether, taken up again in solution in 15 ml of ethanol, and 120 ml of ether added slowly. The slowly precipitated product was dried to give 2.93 g of 1-(3'4'-diethoxybenzyl)-6,7-diisopropoxy-3,4-dihydroisoquinoline hydrochloride. Yield=57%, m.p. 187° C.

Analysis $C_{26}H_{35}NO_4HCl = 462.0$

|  | C % | H % | N % | Cl % |
|---|---|---|---|---|
| Calculated | 67.59 | 7.85 | 3.03 | 7.67 |
| Found | 67.68 | 7.78 | 3.22 | 7.43 |

EXAMPLE 3

(a) N-[2-(3,4-diethoxyphenyl)ethyl]-3,4-di-n-propoxy-phenylacetamide was prepared from 2-(3,4-diethoxyphenyl)-ethylamine and ethyl 3,4-di-n-propoxyphenyl acetate using the process described in Example 1 (a). Yield=77.5%, m.p. 99° C.

Analysis $C_{26}H_{37}NO_5 = 443.6$.

|  | C % | H % | N % |
|---|---|---|---|
| Calculated | 70.40 | 8.41 | 3.16 |
| Found | 70.20 | 8.37 | 3.20 |

(b) 6,7-Diethoxy-1-(3',4'-di-n-propoxybenzyl)-3,4-dihydroisoquinoline hydrochloride The procedure of Example 1 (b) was employed using 26.76 g (0.0602 mole) of N-[2-(3,4-diethoxyphenyl)e-thyl]-3,4-di-n-propoxyphenylacetamide, 350 ml of benzene and 12.3 g (0.081 mole) of phosphorus oxychloride. Yield=85%, m.p. 214° C.

Analysis $C_{26}H_{35}NO_4HCl = 462.0$.

|  | C % | H % | N % | Cl % |
|---|---|---|---|---|
| Calculated | 67.59 | 7.85 | 3.03 | 7.67 |
| Found | 67.29 | 7.76 | 2.98 | 7.79 |

EXAMPLE 4

(a) N-[2-(3,4-di-n-propoxyphenyl)ethyl]-3,4-diethoxy-phenylacetamide was prepared from 2-(3,4-di-n-propoxyphenyl)ethylamine and ethyl 3,4-diethoxyphenylacetate using the process described in Example 1 (a).

(b) 1-(3',4'-Diethoxybenzyl)-6,7-di-n-propoxy-3,4-dihydroisoquinoline hydrochloride The procedure of Example 1 (b) was employed using 34.28 g (0.0773 mole) of N-[2-(3,4-di-n-propoxyphenyl)ethyl]-3,4-diethoxyphenylacetamide, 350 ml of benzene and 15.8 (0.103 mole) of phosphorus oxychloride. Yield=75%, m.p. 210° C.

Analysis $C_{26}H_{35}NO_4HCl = 462.0$.

|  | C % | H % | N % | Cl % |
|---|---|---|---|---|
| Calculated | 67.59 | 7.85 | 3.03 | 7.67 |
| Found | 67.30 | 7.95 | 2.97 | 7.91 |

EXAMPLES 5–8

Preparation of the bases

The following method was employed for Examples 5–8 to convert the hydrochlorides of Examples 1–4 to their corresponding bases:

0.001 mole of the hydrochloride and 30 ml of sodium-dried diethyl ether are introduced into a 100 ml flask, and a stream of nitrogen passed into the suspension. 1 ml of a solution of methanol saturated with ammonia is added at 0° C., the suspension stirred for a few moments and the precipitate drained rapidly e.g. under suction. The solvent is removed under reduced pressure at 20° C. and the product dried in an oven at 40° C. at 0.01 mm pressure. The pressure is then returned to atmospheric pressure under nitrogen.

N.m.r. spectra for Examples 5–8

The n.m.r. spectra were obtained on the products of Examples 5–8 in solution in CDCl₃ at 35° C., using tetramethylsilane as reference.

The chemical shifts which were common to each of the compounds of Examples 5–8 were as follows:

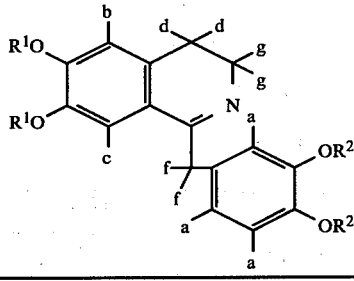

6.8 ppm (multiplet): the three 'a' protons;
6.6 ppm (singlet): the 'b' proton;
7.0 ppm (singlet): the 'c' proton;

-continued

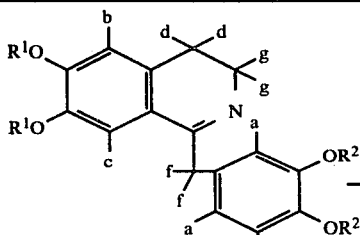

| 3.9 ppm | (multiplet) | | |
|---|---|---|---|
| OR² 1.7 ppm | (2 superimposed sextuplets) | (4H) | —O.CH₂.CH₂.CH₃ |
| 0.95 ppm | (triplet) | (3H) | —O.CH₂.CH₂.CH₃ |
| 1.0 ppm | (triplet) | (3H) | —O.CH₂.CH₂.CH₃ |
| 1.35 ppm | (triplet) | (6H) | —O.CH₂.CH₃ |

2.6 ppm (triplet): the two 'd' protons;
3.7 ppm (triplet): the two 'g' protons;
3.9 ppm (singlet): the two 'f' protons.

EXAMPLE 5

6,7-Diethoxy-1-(3',4'-diisopropoxybenzyl)-3,4-dihydroisoquinoline

Prepared from the compound of Example 1, this product is pale yellow.

n.m.r. characteristics

| 3.95 ppm | (quadruplet) | (4H) | —O.CH₂.CH₃ |
|---|---|---|---|
| 1.3 ppm | (triplet) | (6H) | —O.CH₂.CH₃ |
| 4.4 ppm | (multiplet) | (2H) | —O.CH.(CH₃)₂ |
| 1.2 ppm | (doublet) | (12H) | —O.CH.(CH₃)₂ |

EXAMPLE 6

1-(3',4'-Diethoxybenzyl)-6,7-diisopropoxy-3,4-dihydroisoquinoline

Prepared as a beige product from the compound of Example 2.

n.m.r. characteristics

| 4.1 ppm | (multiplet) | (1H) | —O.CH.(CH₃)₂ |
|---|---|---|---|
| 4.5 ppm | (multiplet) | (1H) | —O.CH.(CH₃)₂ |
| 1.2 ppm | (two overlapping doublets) | (12H) | —O.CH.(CH₃)₂ |
| 4.0 ppm | (quadruplet) | (4H) | —O.CH₂.CH₃ |
| 1.3 ppm | (triplet) | (6H) | —O.CH₂.CH₃ |

EXAMPLE 7

6,7-Diethoxy-1-(3',4'-di-n-propoxybenzyl)-3,4-dihydroisoquinoline

Prepared from the compound of Example 3. M.p. = 79°–80° C.

n.m.r. characteristics

| 4.0 ppm | (multiplet) | (8H) | —O.CH₂.CH₃ and —O.CH₂.CH₂.CH₃ |
|---|---|---|---|
| 1.4 ppm | (multiplet) | (6H) | —O.CH₂.CH₃ |
| 1.75 ppm | (sextuplet) | (4H) | —O.CH₂.CH₂.CH₃ |
| 1.0 ppm | (triplet) | (6H) | —O.CH₂.CH₂.CH₃ |

EXAMPLE 8

1.(3',4'-Diethoxybenzyl)-6,7-di-n-propoxy-3,4-dihydroisoquinoline

Prepared as yellow flakes from the compound of Example 4. M.p. 70.5°–71.5° C.

n.m.r. characteristics

| 3.9 ppm | (multiplet) | (8H) | —O.CH₂.CH₃ & —O.CH₂.CH₂.CH₃ |
|---|---|---|---|
| 1.7 ppm | (2 superimposed sextuplets) | (4H) | —O.CH₂.CH₂.CH₃ |
| 0.95 ppm | (triplet) | (3H) | —O.CH₂.CH₂.CH₃ |
| 1.0 ppm | (triplet) | (3H) | —O.CH₂.CH₂.CH₃ |
| 1.35 ppm | (triplet) | (6H) | —O.CH₂.CH₃ |

EXAMPLE 9

1-(3',4'-Diethoxybenzyl)-6,7-diisopropoxy-1,2,3,4-tetrahydroisoquinoline 14 g (0.0303 mole) of 1-(3',4'-diethoxy-benzyl)-6,7-diisopropoxy-3,4-dihydroisoquinoline hydrochloride was dissolved in 280 ml methanol in a 1 liter 3-necked flask.

The solution was cooled in an ice/water bath and 1.4 g (0.037 mole) of sodium borhydride was added in 2 portions with agitation. The agitation was maintained for half an hour, the solvent removed under reduced pressure and the residue was taken up in 500 ml of diethyl ether. The ethereal solution was washed with water to pH 7, dried over sodium sulphate and the solvent removed under reduced pressure. The oil obtained was left overnight under isopropyl ether to crystallise out the product. 8.6 g of the title product was obtained. Yield=66%, m.p. 76°–80° C.

Analysis C₂₆H₃₇NO₄=427.6.

| | C % | H % | N % |
|---|---|---|---|
| Calculated | 77.03 | 8.72 | 3.28 |
| Found | 77.11 | 8.65 | 3.35 |

EXAMPLE 10

1-(3',4'-Diethoxybenzyl)-6,7-diisopropoxy-1,2,3,4-tetrahydroisoquinoline hydrochloride 81.5 g (0.019 mole) of 1-(3',4'-diethoxybenzyl)-6,7-diisopropoxy-1,2,3,4-tetrahydroisoquinoline was dissolved in 50 ml ethanol. 10 ml of a solution of hydrochloric acid in diethyl ether was added with agitation and cooling in an ice/water bath, (to pH=2). The solvent was removed under reduced pressure, the residue was stirred in suspension in 100 ml of isopropyl ether for a few minutes, excess solvent removed and the product dried to give 8.75 g of the title hydrochloride. Yield=99%. m.p. 158° C.

Analysis C₂₆H₃₇NO₄HCl=464.1.

| | C % | H % | N % | Cl % |
|---|---|---|---|---|
| Calculated | 67.29 | 8.25 | 3.02 | 7.64 |
| Found | 66.87 | 8.17 | 3.27 | 7.76 |

EXAMPLE 11

6,7-Diethoxy-1-(3',4'-diisopropoxybenzyl)-1,2,3,4-tetrahydroisoquinoline hydrochloride 21 g (0.0455 mole) of 6,7-diethoxy-1-(3',4'-diisopropoxybenzyl)-3,4-dihydroisoquinoline hydrochloride was dissolved in 300 ml of methanol in a 1 liter 3-necked flask. The solution was cooled in an ice/water bath and 2.1 g (0.0555 moles) of sodium borhydride was added in two portions with agitation. Stirring was continued for half an hour, the solvent removed under reduced pressure and the residue obtained taken up in 500 ml of diethyl ether. The ethereal solution was washed 3 times with 200 ml of water, dried over sodium sulphate and the solvent removed under reduced pressure. The oil obtained was dissolved in 20 ml of isopropyl ether, and allowed to crystallize. The product was filtered and re-dissolved in 200 ml of diethyl ether, then a solution of hydrochloric acid in diethyl ether added to pH 2. The solvent was removed under reduced pressure and the residue obtained triturated, firstly in isopropyl ether and then in diethyl ether. After drying, 19.5 g of the title hydrochloride was obtained. Yield=92.5%, m.p. 168° C.

Analysis $C_{26}H_{31}NO_4HCl = 464.1$.

|  | C % | H % | N % | Cl % |
|---|---|---|---|---|
| Calculated | 67.29 | 8.25 | 3.02 | 7.64 |
| Found | 67.21 | 8.36 | 3.11 | 7.52 |

EXAMPLE 12

6,7-Diethoxy-1-(3′,4′-diisopropoxybenzyl)-1,2,3,4,-tetrahydroisoquinoline was prepared from the hydrochloride of Example 11 by the general procedure described above for Examples 5–8. The product is obtained as a white crystalline product, m.p. 62° C.

PHARMACEUTICAL COMPOSITIONS

EXAMPLE 13

Tablets are prepared as follows:

| | |
|---|---|
| 1-(3′,4′-Diethoxybenzyl)-6,7-diisopropoxy-3,4-dihydroisoquinoline hydrochloride | 50 mg |
| Excipient (lactose/starch/magnesium stearate) | 150 mg |

The active ingredient is dilued with the lactose, coated with previously prepared 10% starch paste, granulated and dried at low temperature. The granulate is calibrated, magnesium stearate added and compressed to a final weight of 200 mg.

EXAMPLE 14

Tablets are prepared by the method described in Example 13 using the following ingredients:

| | |
|---|---|
| 1-(3′,4′-Diethoxybenzyl)-6,7-diisopropoxy-1,2,3,4-tetrahydroisoquinoline hydrochloride | 100 mg |
| Excipient (lactose/starch/magnesium stearate) | 250 mg |

EXAMPLE 15

An injectable preparation is prepared as follows:

| | |
|---|---|
| 6,7-Diethoxy-1-(3′,4′-diisopropoxybenzyl)-3,4-dihydroisoquinoline hydrochloride | 20 mg |
| Water for injectable preparation | 2 ml |

The active principle is dissolved with slight warming in water and the pH adjusted to 4 with N hydrochloric acid. The solution is filtered under sterile conditions and divided aseptically into previously sterilised ampoules, which are then sealed.

PHARMACOLOGY

In the tests below, the compound papaverine is used for comparative purposes. Papaverine is 1-(3′,4′-dimethoxybenzyl)-6,7-dimethoxy isoquinoline and is employed therapeutically for its spasmolytic and vasodilatory properties.

(1) Acute Toxicity $LD_{50}$ values in mice for several compounds of the invention were obtained by the method of Litchfield and Wilcoxon (J. Pharmacol. (1949), 96.99) after the administration of the test compound by intravenous route (i.v.) in the mouse (CD, males 18–24 g) in a volume of 0.40 ml/20 g of body weight. The mortality is noted 7 days after administration. The results obtained are expressed in milligrammes/kilogram of body weight (mg/kg), and are shown in Table I.

TABLE I

| | Acute Toxicity |
|---|---|
| Product | $LD_{50}$ (mg/kg i.v.) and limits (p = 0.05) |
| Example 1 | 19.0 (17.7 to 20.3) |
| Example 2 | 8.2 ( 6.4 to 10.9) |
| Example 3 | 17.5 (14.6 to 21.0) |
| Example 4 | 13.5 (11.9 to 14.9) |
| Example 10 | 19.0 (16.7 to 21.7) |
| Example 11 | 22.0 (18.3 to 26.4) |

(2) Spasmolytic activity in vitro

The tests are carried out on isolated ileum of the guinea pig surviving in Tyrode liquid, aerated and maintained at 37° C. The products are added 30 seconds before affusion of barium chloride used as contracting agent. The concentrations required to cause inhibition of contraction in 50% of the population ($EC_{50}$) was given in table II compared with papaverine.

TABLE II

| Product | $EC_{50}$ (moles/liter) |
|---|---|
| Papauerine HCl | $9.8 \times 10^{-4}$ |
| Example 1 | $1.1 \times 10^{-5}$ |
| Example 2 | $4.2 \times 10^{-6}$ |
| Example 3 | $3.2 \times 10^{-6}$ |
| Example 4 | $3.7 \times 10^{-6}$ |
| Example 10 | $1.0 \times 10^{-5}$ |
| Example 11 | $6.0 \times 10^{-5}$ |

It can be seen that the spasmolytic activity of each of the compounds tested is greater than that of papaverine.

(3) Cardiovascular Activity

The following parameters were recorded in dogs anaesthetized with chloralose, and under artificial respiration:
mean aortic pressure;
cardiac frequency;
left ventricular contractile force.

The compounds tested were injected intravenously in a dose of from (1/15) to (1/30) of the $LD_{50}$ (i.v.) previoulsy determined in mice.

Results

Whereas papaverine caused a transient hypotension accompanied by tachycardia and an increase of the ventricular contractile force, each of the compounds of the present invention which were tested (compounds of Examples 1,2,3,4,10 and 11) produced a transient hypotension accompanied by a reduction in the amplitude of ventricular contraction.

These results represent a distinct advantage over papaverine because the cardiovascular effect of the compounds is accompanied by a decrease in cardial work and consequently in the exertions and energy requirements of the heart.

We claim:

1. A compound of the formula

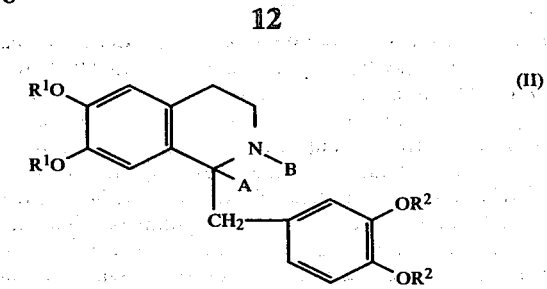

(II)

or a pharmaceutically acceptable acid addition salt thereof, wherein $R^1$ and $R^2$ are different and one is alkyl of 1 to 6 carbon atoms and the other is isopropyl, and A and B together represent a covalent bond.

2. The compound according to claim 1, wherein said alkyl of 1 to 6 carbon atoms is ethyl.

3. The compound according to claim 1, which is a pharmaceutically acceptable acid addition salt.

4. The compound according to claim 2, wherein said salt is a hydrochloride.

5. 6,7-diethoxy-1-(3',4'-diisopropoxybenzyl)-3,4-dihydroisoquinoline, or its hydrochloride.

6. 1-(3',4'-diethoxybenzyl)-6,7-diisopropoxy-3,4-dihydroisoquinoline, or its hydrochloride or ascorbate.

7. A pharmaceutical composition for the treatment of peripheral vascular disease which comprises from 50 to 500 mg of a compound as claimed in claim 1 together with a pharmaceutically acceptable carrier.

* * * * *